(12) United States Patent
Jung et al.

(10) Patent No.: US 11,598,743 B2
(45) Date of Patent: Mar. 7, 2023

(54) SOIL MONITORING SENSOR INCLUDING SINGLE PROBE AND TEMPERATURE COMPENSATION AND METHOD OF OPERATING THE SAME

(71) Applicant: DAMOATECH CO., LTD., Seongnam-si (KR)

(72) Inventors: Hu Min Jung, Hanam-si (KR); Ji Yeong Hong, Tongyeong-si (KR)

(73) Assignee: DAMOATECH CO., LTD., Seongnam-si (KR)

( * ) Notice: Subject to any disclaimer, the term of this patent is extended or adjusted under 35 U.S.C. 154(b) by 88 days.

(21) Appl. No.: 17/215,508

(22) Filed: Mar. 29, 2021

(65) Prior Publication Data

US 2021/0302349 A1  Sep. 30, 2021

(30) Foreign Application Priority Data

Mar. 27, 2020 (KR) .................. 10-2020-0037679

(51) Int. Cl.
*G01R 27/26* (2006.01)
*G01N 27/22* (2006.01)
*G01N 33/24* (2006.01)
*G04F 10/00* (2006.01)

(52) U.S. Cl.
CPC ......... *G01N 27/223* (2013.01); *G01N 27/228* (2013.01); *G01N 33/246* (2013.01); *G04F 10/005* (2013.01)

(58) Field of Classification Search
USPC .......................... 324/634, 640, 643, 664, 689
See application file for complete search history.

(56) References Cited

U.S. PATENT DOCUMENTS

| 4,272,718 A * | 6/1981 | Kashiuchi ............ G01N 27/223 324/668 |
| 5,621,669 A | 4/1997 | Bjornsson |
| 9,077,183 B2 | 7/2015 | Thomas et al. |
| 9,658,178 B2 | 5/2017 | Surman et al. |
| 2015/0330932 A1* | 11/2015 | Kumaran ............ G01N 27/223 324/664 |
| 2017/0239540 A1 | 8/2017 | Chan et al. |

(Continued)

FOREIGN PATENT DOCUMENTS

JP    2016-217795 A    12/2016
KP    10-2016-0006564    1/2016

*Primary Examiner* — Vincent Q Nguyen
(74) *Attorney, Agent, or Firm* — United One Law Group LLC; Kongsik Kim; Jhongwoo Peck

(57) ABSTRACT

Disclosed are a soil monitoring sensor and a method of operating the same. The soil monitoring sensor includes a first probe formed to extend in a first direction, and including a first electrode and a second electrode; a first resonance circuit connected to the first electrode and the second electrode of the first probe, and configured such that a first AC signal is applied thereto; a second resonance circuit having the same impedance as the first resonance circuit, and configured such that a second AC signal is applied thereto; and a determination circuit configured to receive a first electrical signal formed in the first resonance circuit, to receive a second electrical signal formed in the second resonance circuit, and to generate a first determination value for the state of the soil based on the first resonant frequency and the second resonant frequency.

11 Claims, 12 Drawing Sheets

(56) References Cited

U.S. PATENT DOCUMENTS

2017/0241923 A1 8/2017 Chan et al.
2017/0241973 A1 8/2017 Chan et al.
2017/0363551 A9 12/2017 Chan et al.

* cited by examiner

SOIL MONITORING SENSOR INCLUDING SINGLE PROBE AND TEMPERATURE COMPENSATION AND METHOD OF OPERATING THE SAME

CROSS-REFERENCE TO RELATED APPLICATION

This application claims priority to Korean Application No. 10-2020-0037679 filed on Mar. 27, 2020, which is incorporated herein by reference in its entirety.

TECHNICAL FIELD

The present invention relates to a soil monitoring sensor for detecting the state of the soil and a method of operating the same, and more particularly to a soil monitoring sensor for detecting the state of the soil by combining a single probe-type sensor with temperature compensation, a signal processing circuit for enhancing the accuracy of the soil monitoring sensor, and a method of operating the same.

The present invention was derived from the research conducted as part of the Preliminary Startup Package Project sponsored by the Korean Ministry of SMEs and Startups and the Korea Institute of Startup & Entrepreneurship Development [Task Management Number: 10224634, and Task Name: Lawn Management System Using Smart Soil Sensor].

BACKGROUND ART

Conventional methods for measuring the moisture of the soil include a dry basis weight method, a tactile method that evaluates the moisture of the soil based on the texture of each soil, a method of measuring the electrical conductivity of moisture absorbed in the capillary pores of a gypsum block, an unglazed porous cup moisture tensiometer method, and a neutron probe method.

Although a method of determining the weight percentage of moisture using the dry basis weight method has been a representative method of measuring moisture for a long period of time, the procedure thereof is cumbersome and time-consuming, thereby causing inconvenience. The tactile method that evaluates the moisture of the soil based on the texture of each soil is inefficient in that the individual variation of each evaluator is large and considerable training is required. The method of measuring the electrical conductivity of moisture absorbed in the capillary pores of a gypsum block in a relatively simple way has a disadvantage in that the pores of the gypsum block are very fine, so that when the soil moisture tension is low, almost all of the pores are saturated, resulting in unsatisfactory results. Although the unglazed porous cup moisture tensiometer method is also widely adopted for determining an irrigation point, it has a disadvantage in that it does not work in a region where the moisture tension is higher than 1 atmosphere.

The neutron probe method has a disadvantage in that it is not widely used for general purposes because the initial calibration procedure thereof is difficult, the transport, measurement and operation thereof are cumbersome, and the price thereof is considerably high.

Furthermore, there was proposed a time domain reflectometry (TDR) method using the principle in which only the dielectric properties of water according to the rotational motion of water molecules stood out because the movement of ions in the gigahertz field was negligibly reduced. The TDR method is a method of emitting a gigahertz-level high energy frequency to a sensor using an uncovered iron rod inserted into the soil as a condenser and analyzing a time difference or voltage difference according to the number of frequencies reflected according to the degree of permittivity based on the moisture of the soil. The TDR method quantifies the moisture of the soil by simply amplifying reflected electromagnetic waves transformed by a soil condenser using the principle in which electromagnetic waves are transformed by a condenser and reading them using an oscilloscope. Accordingly, disadvantages have been raised in that the necessary equipment is relatively complex and expensive.

For this reason, there is urgently required the development and introduction of an inexpensive soil moisture measurement device that is simpler, has a simpler operation and procedure, and can measure and collect accurate data within a short period of time.

Meanwhile, both the moisture of the soil and electrical conductivity attributable to salts are important parameters as properties of the soil. Korean Patent Application Publication No. 10-2016-0006564 entitled "Device and Method for Measuring Moisture and Salts for Organic Medium" discloses a sensor for measuring the moisture and salts of the soil. In other words, Korean Patent Application Publication No. 10-2016-0006564 discloses a means for allowing three probes to penetrate into the soil, detecting the reflected wave of a single high-frequency wave, and measuring the moisture of the soil through impedance conversion, and determining salts by detecting the reflected wave of the high-frequency component.

U.S. Patent Application Publication No. 2017/0241973 entitled "System and Method for Instantaneously Determining Uniform Distribution of Water, Salinity, Conductivity, Temperature and Other Conditions in Soil" discloses the appearance and system of a soil monitoring sensor that detects the moisture, salts, electrical conductivity, and temperature of the soil.

Meanwhile, Japanese Patent Application Publication No. 2016-217795 entitled "Moisture Sensor and Moisture Measuring Device" discloses a moisture sensor in which a resonance circuit whose resonant frequency changes in response to a change in the equivalent inductance attributable to a change in the moisture content contained in the soil is formed using a moisture sensor having electrodes composed of comb teeth intersecting each other and the resonant frequency generated by the resonance circuit is calculated.

However, even according to the related art, a problem arises in that it is difficult to measure a resonant frequency rapidly and accurately because the process of calculating a resonant frequency by converting a measured amplitude value rather than directly measuring a resonant frequency is complicated. For this reason, a problem arises in that when the moisture content of the soil is measured in real time, noise is generated and thus a measured value is inaccurate.

SUMMARY

The related art is configured to scan the magnitude of an output electrical signal formed in a resonance circuit in response to an input electrical signal by varying the frequency of the input electrical signal applied to the resonance circuit and calculate a frequency in the case of having a maximum size as a resonant frequency. For this reason, the related art is problematic in that it has an error corresponding to the resolution of the variable frequency of the input electrical signal, accuracy is degraded by an indirect method of calculating the resonant frequency by detecting the magnitude of the electrical signal, and a relatively long time is required because the frequency of the input electrical signal needs to be varied.

The present invention was conceived to overcome the above-described problems of the related art, and an object of the present invention is to provide a soil monitoring sensor that generates high-frequency signals in a circuit having a capacitance formed in a probe for a soil monitoring sensor using the soil as a medium and in a circuit having a reference capacitance, respectively, measures and compares frequencies for the high-frequency signals in the two circuits, and quantifies moisture content in the soil, thereby enabling the moisture state of the soil to be more accurately determined in real time.

Furthermore, an object of the present invention is to provide a soil monitoring sensor that is non-destructive and semi-permanently usable, provides the stability of the device, and may significantly reduce manufacturing cost compared to the conventional soil monitoring sensor because it does not require a configuration for varying the frequency of an input electrical signal.

An object of the present invention is to provide a soil monitoring sensor that proposes a circuit and an operating method capable of effectively detecting the shift of a resonant frequency. Furthermore, an object of the present invention is to provide a soil monitoring sensor that may shorten soil moisture detection time because it does not require the process of varying the frequency of an input electrical signal.

An object of the present invention is to provide a soil monitoring sensor that may further include a temperature sensor in order to more accurately detect the moisture content of the soil and may measure precise moisture content by compensating the moisture content of the soil based on the temperature sensor.

The related arts disclosed in above-referenced documents are configured to allow three or four electrodes to penetrate into the soil and monitor the moisture and salts of the soil in adjacent areas (see Korean Patent Application Publication No. 10-2016-0006564 and U.S. Patent Application Publication No. 2017/0241973), or are configured to use two electrodes and increase a contact area where the soil between the two electrodes is located (see Japanese Patent Application Publication No. 2016-217795). These related arts are problematic in that the range of the soil to be monitored is limited or accuracy is degraded due to the shape of a probe.

A soil monitoring sensor according to the present invention may monitor characteristic parameters such as the moisture and salts of the soil surrounding the outer periphery of a probe by means of a single-pole probe. Accordingly, another object of the present invention is to provide a soil monitoring sensor that does not limit the range of the soil to be monitored and is applicable to the soils in various environments.

According to an aspect of the present invention, there is provided a soil monitoring sensor including: a first probe formed to extend in a first direction so as to penetrate into the soil, and including a first electrode and a second electrode; a first resonance circuit connected to the first electrode and the second electrode of the first probe, and configured such that a first alternating current (AC) signal is applied thereto; a second resonance circuit having the same impedance as the first resonance circuit, and configured such that a second AC signal, which is a reference AC signal and has the same characteristic as the first AC signal, is applied thereto; and a determination circuit configured to receive a first electrical signal formed in the first resonance circuit, to receive a second electrical signal formed in the second resonance circuit, and to generate a first determination value for the state of the soil based on the first resonant frequency of the first electrical signal and the second resonant frequency of the second electrical signal. In this case, the first electrode includes a conductor surrounding the outside of the first probe, comes into contact with the soil, and detects information about the state of the soil.

The soil monitoring sensor may further include a temperature sensor coupled to at least any one of the first electrode and the second electrode of the first probe. The determination circuit may be further configured to generate a second determination value for the state of the soil by compensating the first determination value based on a temperature measured by the temperature sensor.

The second electrode may be disposed inside the first probe, may protrude from the tip of the first probe to come into contact with the soil, and may be connected to the ground node of at least one of the first resonance circuit, the second resonance circuit, and the determination circuit to function as a ground electrode.

The first electrode may come into contact with the soil outside the first probe, and an area in which the first electrode comes into contact with the soil may be larger than an area in which the second electrode comes into contact with the soil.

The gap between the first electrode and the second electrode may be filled with an insulator, or the first electrode and the second electrode may be spaced apart from each other so that an empty space is formed inside the first probe.

The determination circuit may be further configured to: detect a quantitative change in the first resonant frequency of the first electrical signal formed in the first resonance circuit based on a capacitance formed between the soil surrounding and being in contact with the first electrode and the first electrode due to moisture contained in a region of the soil, surrounding and being in contact with the first electrode, adjacent to the first electrode; and generate the first determination value for the state of the soil based on the detected quantitative change in the first resonant frequency. In this case, the determination circuit may generate the first determination value for the state of the soil based on the quantitative change in the first resonant frequency, and may generate the second determination value by compensating the first determination value based on the measured temperature.

The determination circuit may be further configured to: detect a difference between the second resonant frequency, which is a reference resonant frequency of the second electrical signal formed in the second resonance circuit under the influence of the second AC signal applied to the second resonance circuit, and the first resonant frequency; and generate the first determination value for the state of the soil based on the difference between the second resonant frequency and the first resonant frequency. In this case, the determination circuit may generate the first determination value for the moisture contained in the soil based on the difference between the second resonant frequency and the first resonant frequency, and may generate the second determination value by compensating the first determination value based on the measured temperature.

In this case, the determination circuit may be further configured to, when the difference between the second resonant frequency and the first resonant frequency is equal to or higher than a first threshold value, consider that a significant change has occurred in the first resonant frequency and determine the state of the soil. For example, when the difference between the first resonant frequency and the second resonant frequency is equal to or larger than a first threshold value, it may be determined with respect to the state of the soil that the moisture contained in the soil is equal to or larger than an effective threshold value.

The determination circuit may include: an operator configured to obtain the difference between the first resonant frequency and the second resonant frequency; a low-pass filter connected to the output terminal of the operator, and configured to remove a high-frequency component; and a time-to-digital converter connected to the output terminal of the low-pass filter, and configured to digitally count the frequency of a third frequency component signal corresponding to the difference between the first resonant frequency and the second resonant frequency.

According to another aspect of the present invention, there is provided a soil monitoring method including: applying, by a first oscillator, a first alternating current (AC) signal to the first electrode and the second electrode of a first probe via a first resonance circuit connected to the first electrode and the second electrode of the first probe formed to extend in a first direction so as to penetrate into the soil and including the first electrode and the second electrode; applying, by a second oscillator having the same characteristic as the first oscillator, a second AC signal, which is a reference AC signal, to a second resonance circuit having the same impedance as the first resonance circuit; receiving, by a determination circuit, a first electrical signal formed in the first probe and the first resonance circuit under the influence of the first AC signal; receiving, by the determination circuit, a second electrical signal formed in the second resonance circuit under the influence of the second AC signal applied to the second resonance circuit; and generating, by the determination circuit, a first determination value for the state of the soil in contact with the first electrode surrounding the outside of the first probe based on the first resonant frequency of the first electrical signal and the second resonant frequency of the second electrical signal.

In this case, the soil monitoring method may further include: measuring, by a temperature sensor coupled to any one of the first electrode and the second electrode of the first probe, the temperature of the soil; and generating a second determination value for the state of the soil by compensating the first determination value based on the temperature measured by the temperature sensor. In this case, the determination circuit may generate the first determination value for the state of the soil based on the difference between the second resonant frequency and the first resonant frequency, and may generate the second determination value by compensating the first determination value based on the measured temperature of the soil.

The generating a first determination value may include: detecting a quantitative change in the first resonant frequency of the first electrical signal formed in the first resonance circuit based on a capacitance formed between the soil, surrounding and being in contact with the first electrode, and the first electrode due to moisture contained in a region of the soil, surrounding and being in contact with the first electrode, adjacent to the first electrode; and generating the first determination value for the state of the soil based on the detected quantitative change in the first resonant frequency.

The soil monitoring method may further include detecting, by the determination circuit, the difference between the first resonant frequency and the second resonant frequency.

In this case, the generating a first determination value may include generating the first determination value for moisture contained in a region of the soil, in contact with the first electrode, adjacent to the first electrode based on the difference between the first resonant frequency and the second resonant frequency.

The detecting the difference between the first resonant frequency and the second resonant frequency may include: obtaining, by an operator circuit, the difference between the first resonant frequency and the second resonant frequency; removing, by a low-pass filter connected to the output terminal of the operator circuit, a high-frequency component of an output signal of the operator circuit; and generating, by a time-to-digital converter connected to the output terminal of the low-pass filter, the difference between the first resonant frequency and the second resonant frequency as a digital value by digitally counting the frequency of a third frequency component signal corresponding to the difference between the first resonant frequency and the second resonant frequency.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Other objects and features of the present invention in addition to the above-described objects will be apparent from the following description of embodiments with reference to the accompanying drawings. Embodiments of the present invention will be described in detail below with reference to the accompanying drawings. In the following description, when it is determined that a detailed description of a related known component or function may unnecessarily make the gist of the present invention obscure, it will be omitted. Soil monitoring sensors and methods of operating the same according to embodiments of the present invention will be described in detail below with reference to FIGS. 1 to 12.

Figure 1:
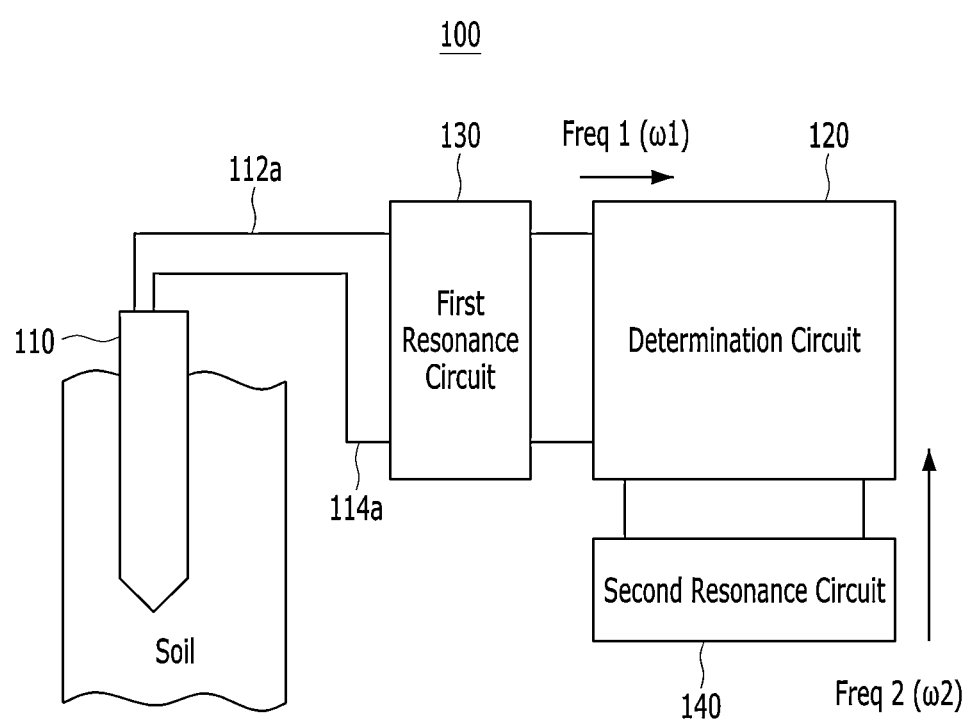
FIG. 1 is a diagram showing a soil monitoring sensor according to an embodiment of the present invention.

FIG. 1 is a diagram showing a soil monitoring sensor 100 according to an embodiment of the present invention.

Referring to FIG. 1, the soil monitoring sensor 100 according to the present embodiment includes a first probe 110, a first resonance circuit 130, a second resonance circuit 140, and a determination circuit 120.

The first probe 110 includes a first electrode 112 (not shown in FIG. 1) and a second electrode 114 (not shown in FIG. 1). The first resonance circuit 130 is electrically connected to the first electrode 112 via a first electrode wiring 112a, and the ground node of the second resonance circuit 130 is electrically connected to the second electrode 114 via a second electrode wiring 114a.

The first probe 110 is formed to extend in a first direction to penetrate into the soil. A first AC signal is applied to the first resonance circuit 130 and the first electrode 112 of the first probe 110. In this case, a first oscillator 132 (not shown in FIG. 1) configured to apply the first AC signal may be connected in parallel and disposed between the first resonance circuit 130 and the determination circuit 120, and may be implemented by being included in any one of the first resonance circuit 130 and the determination circuit 120.

The second resonance circuit 140 has the same impedance characteristic as the first resonance circuit 130. A second AC signal that is a reference AC signal and has the same characteristic as the first AC signal is applied to the second resonance circuit 140. A second oscillator 142 (not shown in FIG. 1) configured to apply the second AC signal may be connected in parallel and disposed between the second resonance circuit 140 and the determination circuit 120, and may be implemented by being included in any one of the second resonance circuit 140 and the determination circuit 120.

The determination circuit 120 receives a first electrical signal formed in the first resonance circuit 130, receives a second electrical signal formed in the second resonance circuit 140, and generates a first determination value for the state of the soil based on the first resonant frequency $\omega 1$ of the first electrical signal and the second resonant frequency $\omega 2$ of the second electrical signal. In this case, the state of the soil may include at least one of moisture contained in the soil, the salts of the soil (the salinity of the soil), and the electrical conductivity (EC) of the soil.

Figure 3:
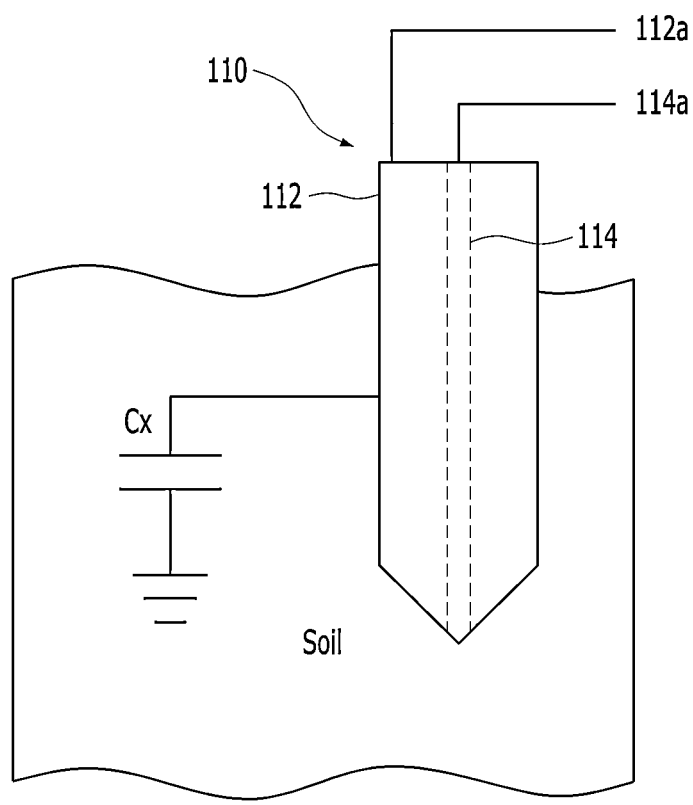
FIG. 3 is a diagram illustrating the configuration and operation principle of the single-pole probe of a soil monitoring sensor according to an embodiment of the present invention.
Figure 4:
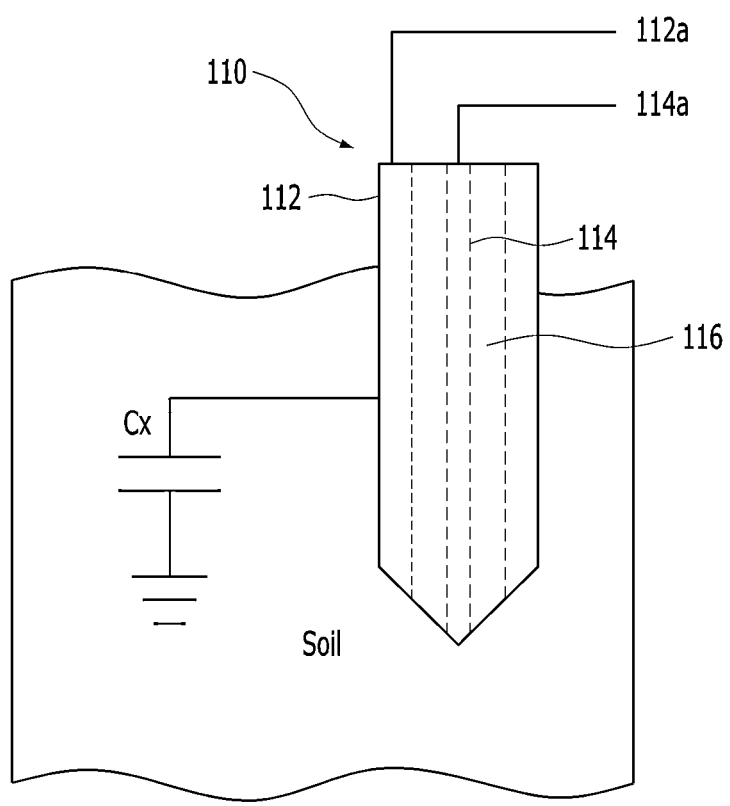
FIG. 4 is a diagram illustrating the internal configuration and operation principle of the single-pole probe of a soil monitoring sensor according to an embodiment of the present invention.

The first electrode 112 includes a conductor surrounding the outside of the first probe 110 as shown in FIGS. 3 and 4, and functions as an electrode that comes into contact with the soil and receives and detects information about the state of the soil.

Figure 2:
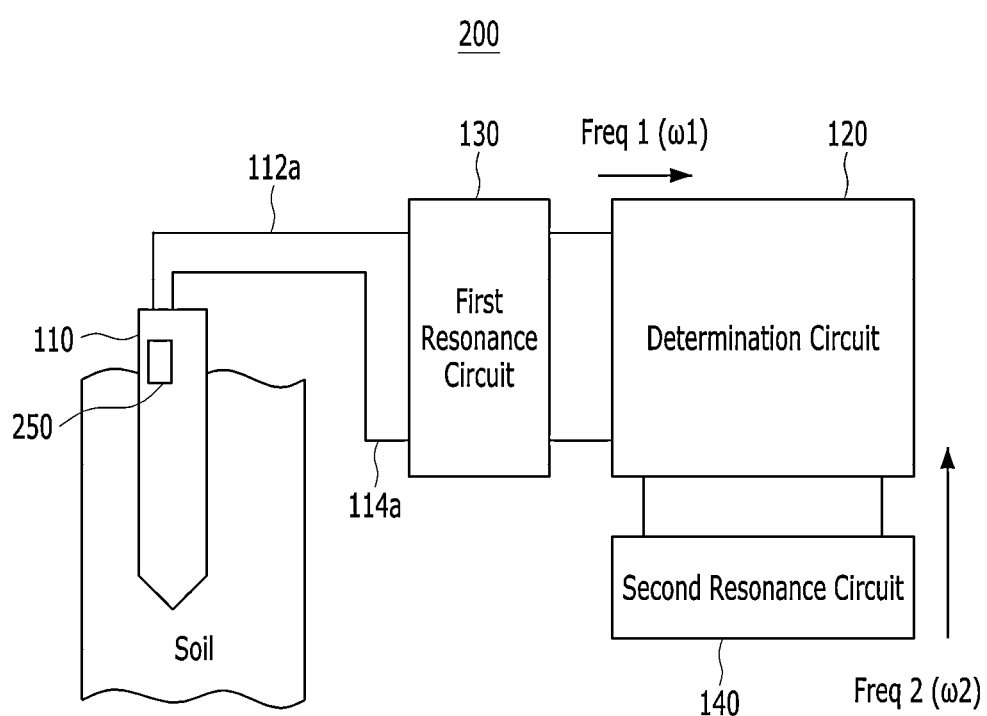
FIG. 2 is a diagram showing a soil monitoring sensor according to an embodiment of the present invention.

FIG. 2 is a diagram showing a soil monitoring sensor 200 according to an embodiment of the present invention. Referring to FIG. 2, the soil monitoring sensor 200 includes a first probe 110, a first resonance circuit 130, a second resonance circuit 140, and a determination circuit 120.

Since the first resonance circuit 130, second resonance circuit 140, and first probe 110 of FIG. 2 have been sufficiently described based on the items shown in FIG. 1, redundant descriptions thereof will be omitted. The descriptions of the operation of the determination circuit 120 of FIG. 2 that overlap those of the operation of the determination circuit 120 of FIG. 1 will be omitted.

The soil monitoring sensor 200 of FIG. 2 may further include a temperature sensor 250 coupled to the first probe 110. In this case, the temperature sensor 250 may be coupled to at least one of the first electrode 112 and the second electrode 114. The determination circuit 120 may generate a second determination value for the state of the soil by compensating a first determination value for the state of the soil based on a temperature measured by the temperature sensor 250. In this case, although the first determination value and the second determination value are introduced for ease of description, the second determination value may be generated by applying a determination criterion, based on a temperature measured by the temperature sensor 250, to a first electrical signal (and/or a second electrical signal) received by the determination circuit 120. Since it is known that the moisture or electrical conductivity (EC) of the soil varies in proportion or inverse proportion to a temperature, the second determination value for the moisture and/or electrical conductivity of the soil compensated based on the temperature may be generated by applying moisture and/or electrical conductivity (EC) criteria based on temperature to the first electrical signal (and/or the second electrical signal) received by the determination circuit 120.

FIG. 3 is a diagram illustrating the configuration and operation principle of the single-pole probe 110 of a soil monitoring sensor 100 or 200 according to an embodiment of the present invention.

The first probe 110 includes a first electrode 112 and a second electrode 114. The first electrode 112 is a conductor, and is disposed to surround the outside of the first probe 110 and connected to the first resonance circuit 130 via a first electrode wiring 112a.

The second electrode 114 may be disposed inside the first probe 110, may protrude from the tip of the first probe 110 to come into contact with the soil, and may function as a ground electrode by being electrically connected to the ground node of at least one of the first resonance circuit 130, the second resonance circuit 140, and the determination circuit 120. The second electrode 114 may be electrically connected to the ground node of at least one of the first resonance circuit 130, the second resonance circuit 140, and the determination circuit 120 via a second electrode wiring 114a.

The first electrode 112 comes into contact with the soil outside the first probe 110. The area in which the first electrode 112 comes into contact with the soil may be larger than the area in which the second electrode 114 comes into contact with the soil. In other words, the first electrode 112 may come into contact with the soil surrounding the first probe 110 in a large area because it is formed to surround the outer periphery of the first probe 110, and the second electrode 114 may function as a ground electrode while in contact with the soil at the tip of the first probe 110.

The determination circuit 120 may detect a quantitative change in the first resonant frequency $\omega 1$ of a first electrical signal formed in the first resonance circuit 130 based on the capacitance Cx formed between the reference-ground and the first electrode 112. The capacitance Cx may be understood to be formed by the interaction between the soil surrounding and being in contact with the first electrode 112 and the first electrode 112 due to moisture contained in the region of the soil surrounding and being in contact with the first electrode 112 near the first electrode 112. The determination circuit 120 may generate a first determination value for the state of the soil based on the detected quantitative change in the first resonant frequency ω1. In this case, the determination circuit 120 may generate the first determination value for the state of the soil based on the quantitative change in the first resonant frequency and may generate the second determination value by compensating the first determination value based on the temperature measured by the temperature sensor 250. In general, it is known that when a temperature changes, information on the state (moisture, salts, and/or electrical conductivity) of the soil determined even for the value of the same first resonant frequency ω1 may vary.

The determination circuit 120 may determine whether the moisture content contained in the soil surrounding the outside of the first electrode 112 of the first probe 110 has a significant value by taking into consideration a capacitance value 126 attributable to the moisture contained in the soil substantially in the deep or inner part of the soil and a capacitance value 125 for the soil itself excluding moisture contained in the soil substantially in the part of the soil near the surface of the soil through a calibration process.

In this case, the determination circuit 120 may detect the moisture content of the soil by comparing the difference between a first resonant frequency ω1 which is generated by a capacitance value Cx attributable to the moisture contained in the soil substantially in the deep or inner part of the soil and a second resonant frequency ω2, which is a reference resonant frequency, with a minimum threshold value.

The single-pole probe 110 of FIG. 3 forms a capacitance Cx via the first electrode 112 that interacts with the soil surrounding the outside thereof, and the soil monitoring sensor 100 or 200 detects a change in the first resonant frequency ω1 based on the capacitance Cx. Compared with conventional 3-pole and 4-pole soil monitoring sensors, the soil monitoring sensors 100 and 200 using the single-pole probe 110 according to the present invention may measure the moisture of the soil in a wide area as well as the moisture in a local range. The conventional multi-pole soil monitoring sensors form capacitance only for a local part of the soil located between multiple poles, whereas the soil monitoring sensors 100 and 200 of the present invention may come into contact with the soil in a larger area and measure moisture, salts, and electrical conductivity. In other words, when the measured values of the conventional multi-pole soil monitoring sensors vary depending on the penetrated positions of the soil, the soil monitoring sensors 100 and 200 of the present invention provide a means for monitoring a state in the soil in a manner robust to the position where and/or how deep the single-pole probe 110 penetrates into the soil. Meanwhile, although there have been soil monitoring sensors having a single-pole probe so far, they are problematic in that it takes a long time to scan a wide range of frequencies or in that the accuracy of measurement is poor because it is difficult to measure the amplitude of a reflected wave.

The soil monitoring sensors 100 and 200 of the present invention provide a robust measurement result for the position where the soil is penetrated using the single-pole probe 110, frequency characteristics may be detected at one time without the need to scan multiple frequencies, and it is not necessary to separately detect the amplitude of a resonance signal because the difference between resonant frequencies is detected in order to measure moisture in the soil. Therefore, they may reduce the cost of measurement, shorten the time, and improve the accuracy of measurement.

Furthermore, the soil monitoring sensors 100 and 200 according to the embodiments of the present invention may detect the difference between resonant frequencies in an integrated circuit chip including the soil monitoring sensor 100 or 200, may convert the difference between the resonant frequencies into the amplitude of an analog signal (in proportion to information about the state of the soil corresponding to the difference between the resonant frequencies), and may output the amplitude of the analog signal to the outside in order to support compatibility with the peripheral interface of the conventional amplitude-based soil monitoring sensor. In this case, the peripheral interface may receive a signal in which the amplitude of an analog signal is converted like the conventional sensors, and may receive information about the state of the soil from the soil monitoring sensors 100 and 200 of the present invention. In this case, there is no need for an external device or a separate circuit configuration, and the cost may be reduced even for communication with the peripheral interface of the conventional sensor.

A frequency-to-voltage converter circuit may be used as a means for converting the difference between resonant frequencies into a voltage and outputting it as an analog signal. In this case, in order to remove noise, a filter capacitor may be added. Additionally, when the capacitance of the filter capacitor needs to be large, a capacitor connection pin exposed to the outside may be provided such that the exterior capacitor can be connected to the soil monitoring sensor 100 or 200.

Meanwhile, the accuracy of measurement may be further improved by taking into consideration first estimation information obtained by detecting the difference between the resonant frequencies and then estimating the state of the soil, and second estimation information obtained by detecting the amplitude of a resonance signal and then estimating the state of the soil in an integrated manner. Information about the state of the soil in which the first estimation information is compensated using the second estimation information may be generated, and vice versa.

FIG. 4 is a diagram illustrating the internal configuration and operation principle of the single-pole probe 110 of a soil monitoring sensor 100 or 200 according to an embodiment of the present invention.

Referring to FIG. 4, the first probe 110 includes a first electrode 112 and a second electrode 114. The descriptions of the first electrode 112, a first electrode wiring 112a, a second electrode 114a, and a second electrode wiring 114a that overlap those of the embodiment of FIG. 3 will be omitted.

A description of a capacitance Cx formed by the first electrode 112 relative to the reference-ground through interaction with the soil surrounding the outside of the first electrode 112 can also be omitted because it is very similar to that of the embodiment of FIG. 3.

A gap 116 is formed between the first electrode 112 and the second electrode 114. The gap 116 may be filled with an insulator, or an empty space corresponding to the gap 116 may be formed inside the first probe 110 by spacing the first electrode 112 and the second electrode 114 apart from each other. In addition, a part of the gap 116 may be filled with an insulator, and the remaining part thereof may be formed as an empty space.

Figure 5:
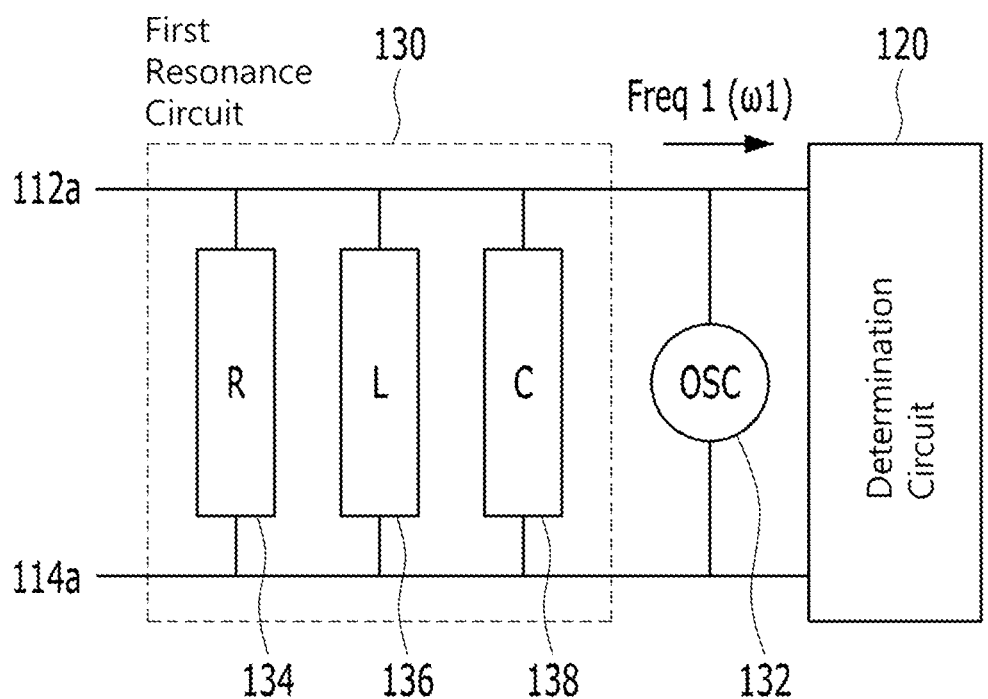
FIG. 5 is a diagram illustrating the interaction between a first resonance circuit and a determination circuit connected to the single-pole probe of a soil monitoring sensor according to an embodiment of the present invention.

FIG. 5 is a diagram illustrating the interaction between a first resonance circuit 130 and a determination circuit 120 connected to the single-pole probe 110 of a soil monitoring sensor 100 or 200 according to an embodiment of the present invention.

Figure 6:
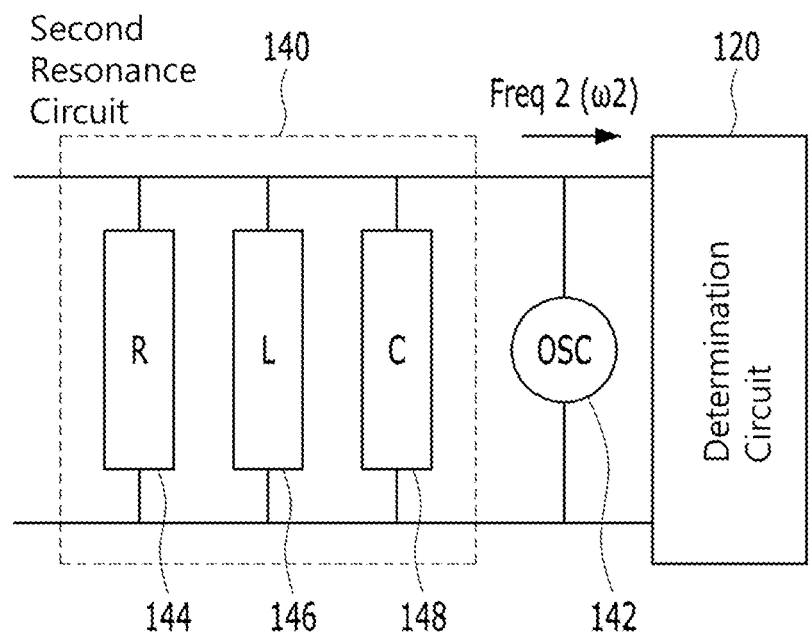
FIG. 6 is a diagram illustrating the interaction between a second resonance circuit, which is the reference resonance circuit of the soil monitoring sensor according to the embodiment of the present invention, and the determination circuit.

FIG. 6 is a diagram illustrating the interaction between a second resonance circuit 140, which is the reference resonance circuit of the soil monitoring sensor 100 or 200 according to the embodiment of the present invention, and the determination circuit 120.

Referring to FIGS. 5 and 6 together, the determination circuit 120 may detect the difference between a second resonant frequency ω2, which is the reference resonant frequency of a second electrical signal formed in the second resonance circuit 140 under the influence of a second AC signal applied to the second resonance circuit 140, and a first resonant frequency ω1. The determination circuit 120 may generate a first determination value for the state of the soil based on the difference between the second resonant frequency ω2 and the first resonant frequency ω1. In this case, the determination circuit 120 may generate a first determination value for the moisture contained in the soil based on the difference between the second resonant frequency ω1 and the first resonant frequency ω1, and may generate a second determination value by compensating the first determination value based on the temperature measured by the temperature sensor 250.

In this case, when the difference between the second resonant frequency ω2 and the first resonant frequency ω1 is equal to or larger than a first threshold value, the determination circuit 120 may consider that a significant change has occurred in the first resonant frequency ω1 and determine the state of the soil. For example, when the difference between the second resonant frequency ω2 and the first resonant frequency ω1 is equal to or larger than the first threshold value, the state of the soil may be determined to be the state in which the moisture contained in the soil is equal to or larger than an effective threshold value.

Alternatively, the relationship between the moisture of the general soil and the difference value between resonant frequencies may be stored as data in memory or a database based on the temperature measured by the temperature sensor 250, and a determination value for the currently measured moisture of the soil may be generated with reference to data stored in the memory or database based on the difference value between the detected resonant frequencies and temperature.

The first resonance circuit 130 of FIG. 5 may be connected to the first electrode 112 of the first probe 110 via the first electrode wiring 112a. The second electrode 114 may be electrically connected to the ground nodes of the first resonance circuit 130, the first oscillator 132, and the determination circuit 120 via the second electrode wiring 114a. Although an embodiment in which the first oscillator 132 is disposed between the first resonance circuit 130 and the determination circuit 120 is illustrated in FIG. 5, the first oscillator 132 may be included in any one of the resonance circuit 130 and the determination circuit 120 in another embodiment of the present invention. The first oscillator 132 applies a first AC signal to the first resonance circuit 130, and the first AC signal has a predetermined oscillation frequency. The first AC signal is applied to the impedance of the first resonance circuit 130, and thus a first electrical signal resonated by the first resonance circuit 130 is formed in the first resonance circuit 130. In this case, the first resonant frequency ω1 of the first electrical signal is determined.

The first oscillator 132 also applies the first AC signal to the first electrode 112 and the second electrode 114, connected to the first resonance circuit 130, via the first resonance circuit 130. A capacitance Cx is formed between the first electrode 112 and the ground due to the interaction with the soil surrounding the first electrode 112, and the capacitance Cx affects the combined impedance of the first resonance circuit 130. The capacitance Cx is formed based on the moisture of the soil, and the first resonant frequency ω1 may be determined under the influence of the capacitance Cx. When the first resonant frequency ω1 of the first electrical signal is determined, the first electrical signal is transmitted to the determination circuit 120 so that the determination circuit 120 detects the first resonant frequency ω1, or the difference between the first resonant frequency ω1 and the second resonant frequency ω2 may be detected.

Furthermore, the first resonance circuit 130 includes a first inductor 136 and a first capacitor 138. Although the first inductor 136 may have the form of a coil, it may be implemented in the form of a semiconductor pattern having a controllable inductance. Referring to FIG. 5, a first parasitic resistor 134 formed in the first resonance circuit 130 is illustrated. According to an embodiment of the present invention, a resistor R' (not shown) may be additionally disposed for the purpose of balancing between the first resonance circuit 130 and other circuits to be described later.

Meanwhile, the soil monitoring sensor 100 of the present invention may be implemented by forming the first resonance circuit 130, the first oscillator 132, the second resonance circuit 140, the second oscillator 142, and the determination circuit 120 as an integrated circuit (IC). In this case, the integrated circuit may be connected with the first electrode 112 and second electrode 114 of the first probe 110 via the first electrode wiring 112a and the second electrode wiring 114a functioning as an interface port.

When the determination circuit 120 of the soil monitoring sensor is fabricated as a single chip as described above, the first resonance circuit 130 on the sensor side and the second resonance circuit 140, which is a reference resonance circuit, are disposed close to each other and composed of the same type of devices in the same semiconductor wafer. Accordingly, the measurement error attributable to semiconductor process variation may be reduced, and thus the moisture content in the soil may be accurately determined in real time.

The first resonant frequency ω1 of the first electrical signal may be determined based on the moisture contained in the soil surrounding the first electrode 112 of the first probe 110.

In other words, due to a change in the capacitance Cx formed between the first electrode 112 and the ground due to the interaction between the soil surrounding the first electrode 112 of the first probe 110 and the first electrode 112, the impedance of the first resonance circuit 130 and the capacitance Cx formed in the first probe 110 are connected in parallel to each other, and thus a change of a combined impedance having an arithmetically summed capacitance can be determined. The first AC signal is applied to the impedance to form a first electrical signal having a first resonant frequency ω1 in the first resonance circuit 130. Likewise, a first electrical signal having a first resonant frequency ω1 is formed in the first probe 110 including the first electrode 112 and the second electrode 114.

The second resonance circuit 140 is designed to have the same impedance as the first resonance circuit 130. In particular, a second inductor 146 and a second capacitor 148 in the second resonance circuit 140 may be designed to have the same values as the first inductor 136 and the first capacitor 138 in the first resonance circuit 130. In addition, the second resonance circuit 140 may be disposed close to the first resonance circuit 130 in the semiconductor wafer so that they can be less affected by process variation during fabrication of semiconductor.

Meanwhile, although a parasitic resistance component 144 in the second resonance circuit 140 is illustrated, a resistor R' (not shown) may be additionally included to allow the impedances of the first resonance circuit 130 and the second resonance circuit 140 to accurately match each other and improve balancing according to an embodiment of the present invention.

A second AC signal applied by the second oscillator 142 is applied to the second resonance circuit 140. The applied second AC signal is applied to the impedance of the second resonance circuit 140 to form a second electrical signal in the second resonance circuit 140. The second AC signal is a reference AC signal, and thus a second electrical signal formed in the second resonance circuit 140 is a reference electrical signal. In this case, the second electrical signal has a second resonant frequency ω2, which is a reference resonant frequency. The second electrical signal is formed while resonating in the second resonance circuit 140 in such a manner that the second AC signal having the natural frequency of the second oscillator 142 and the impedance of the second resonance circuit 140 are combined with each other. Although the second oscillator 142 is designed to have the same characteristics as the first oscillator 132 for ease of description, it is more important that the first resonant frequency ω1 and the second resonant frequency ω2 are matched to be the same by the impedance matching of the first resonance circuit 130 and the second resonance circuit 140 while the state of the soil is not detected.

Since the second resonance circuit 140 is not exposed to the outside, the electrical characteristics of the second resonance circuit 140 are not affected regardless of the presence or absence of moisture contained in the soil. Accordingly, the second electrical signal may maintain the second resonant frequency ω2, which is a reference resonant frequency, regardless of the presence or absence of moisture contained in the soil.

As shown in FIGS. 5 and 6, the first electrical signal having the first resonant frequency ω1 formed in the first resonance circuit 130 and the second electrical signal having the second resonant frequency ω2 formed in the second resonance circuit 140 are transmitted to the determination circuit 120. The operations of the second oscillator 142 and the second resonance circuit 140 may also be controlled by a control unit/controller/processor (not shown) included in the determination circuit 120.

The determination circuit 120 may receive the first electrical signal having the first resonant frequency ω1 formed in the first resonance circuit 130, may receive the second electrical signal having the second resonant frequency ω2 formed in the second resonance circuit 140, and may determine the moisture content contained in the soil surrounding the outside of the first electrode 112 of the first probe 110 based on the first resonant frequency ω1 and the second resonant frequency ω2.

In this case, the determination circuit 120 may determine the moisture content contained in the soil surrounding the outside of the first electrode 112 of the first probe 110 through the value of a change in the first resonant frequency ω1.

The determination circuit 120 may detect a quantitative change in the first resonant frequency ω1 of the first electrical signal formed in the first resonance circuit 130 based on the capacitance Cx formed according to the moisture content contained in the soil surrounding the outside of the first electrode 112 of the first probe 110, and may measure the moisture content contained in the soil surrounding the outside of the first electrode 112 of the first probe 110 based on the detected quantitative change in the first resonant frequency ω1.

More specifically, the capacitance may be represented by the equation below:

$$C = \varepsilon \cdot \frac{s}{d} = \varepsilon_r \cdot \varepsilon_0 \cdot \frac{s}{d} \tag{1}$$

where C is the capacitance, E is a permittivity constant, S is the area of opposite electrodes, and d is the distance between the electrodes.

The permittivity constant E and the capacitance C are proportional to each other. Furthermore, $\varepsilon_0 = 8.854 \ast 10 - 12 F/m$ (the permittivity of vacuum)

$\varepsilon_r$ =Relative Permittivity

The permittivity constant ε uses the relative permittivity $\varepsilon_r$, which is a ratio with respect to the permittivity $\varepsilon_0$ of specific vacuum, as a characteristic value.

Since the relative permittivity of air is similar to that of vacuum and the relative permittivity $\varepsilon_r$ of water is about 80 and relatively much larger than that of air and soil particles, the permittivity constant of soil is significantly affected by the moisture content of the soil. Since the voids in the soil are also similar to the air, they do not significantly affect a change in the relative permittivity attributable to the moisture content. Meanwhile, the relative permittivity of vacuum is always maintained at 1 regardless of a change in temperature, but the permittivity of water decreases as the temperature increases. Therefore, as the amount of water contained in the soil increases at a constant temperature, the permittivity constant of the soil will increase, and thus the capacitance of the soil will increase.

When the temperature changes, the permittivity of water will change accordingly, and thus it is necessary to compensate the moisture content contained in the soil based on the change in temperature.

The resonant frequency f of a circuit configured to detect moisture contained in the soil and a reference circuit may be represented by the equation below:

$$f = \frac{1}{2\pi \cdot \sqrt{L \cdot C}} \tag{2}$$

where L is inductance and C is capacitance. The resonant frequency f and the capacitance C are inversely proportional to each other. Therefore, as the capacitance of the soil increases, the resonant frequency f decreases.

In the circuit configured to detect moisture contained in the soil, as the moisture content contained in the soil surrounding the outside of the first electrode 112 of the first probe 110 increases, the capacitance Cx that is coupled to the first probe 110 increases. Accordingly, the first resonant frequency ω1 of the first electrical signal formed by the combined capacitance of the first resonance circuit 130 that is connected in parallel and added arithmetically will decrease.

The first electrode 112 and second electrode 114 of the first probe 110 configured to measure the moisture content of the soil are connected only to the first resonance circuit 130 via the first electrode wiring 112a and the second electrode wiring 114a, but are not connected to the second resonance circuit 140 of the reference resonance circuit. The first resonant frequency ω1 of the first electrical signal may be determined based on the moisture contained in the soil surrounding the outside of the first electrode 112 of the first probe 110. More specifically, the impedance and capacitance of the first resonance circuit 130 are connected in parallel to each other due to a change in capacitance Cx formed according to the moisture content contained in the soil surrounding the outside of the first electrode 112 of the first probe 110. Accordingly, as the combined impedance changes in that the impedance and the capacitance Cx are connected and added arithmetically, the first resonant frequency ω1 of the first electrical signal also changes.

Meanwhile, unlike the first resonance circuit 130, the second resonance circuit 140 is not connected to the first probe 110 configured to measure the moisture content of the soil, and thus the second resonance circuit 140 maintains the second resonant frequency ω2 regardless of the presence or absence of moisture in the soil.

In this case, the second resonance circuit 140 may generate the second electrical signal having the second resonant frequency ω2 based on the capacitance using air as a medium.

Therefore, when the difference in frequency between the second electrical signal of the second resonance circuit 140 and the first electrical signal of the first resonance circuit 130 is detected, it may be determined whether the first resonant frequency ω1 of the first resonance circuit 130 has been shifted from the resonant frequency ω2, and also the degree of shift may be quantitatively analyzed if it has been shifted.

The reference resonance circuit may track a change in the first resonant frequency ω1 generated in the first resonance circuit 130, may remove the noise added to the first resonant frequency ω1 measured by the determination circuit 120 in real time, and may accurately measure the degree of change in the first resonant frequency ω1.

When the first probe 110 is inserted into the soil, the first resonant frequency ω1 changes due to the influence of the capacitance Cx formed between the first electrode 112 and the ground due to the interaction with the soil surrounding the outside of the first electrode 112 via the soil. In this case, in the considerably dry soil, e.g., dry sand, or dry wasteland, a change in the first resonant frequency ω1 is not large. In contrast, in the case of the soil containing moisture, a relatively large change in the first resonant frequency ω1 is detected.

The determination circuit 120 may detect the difference between the second resonant frequency ω2, which is the reference resonant frequency of the second electrical signal formed in the second resonance circuit 140 under the influence of the second AC signal applied to the second resonance circuit 140, and the first resonant frequency ω1, and may determine the moisture content contained in the soil from the first probe 110 based on the difference (ω2−ω1) between the second resonant frequency and the first resonant frequency.

Meanwhile, when a foreign material such as a conductor enters the soil in the first probes 110, or when the soil contains a large amount of moisture, e.g., when the soil becomes muddy, the electrical characteristic between the first electrode 112 of the first probe 110 and the ground may significantly deviate from an initially assumed range. In addition, when the moisture content contained in the soil is excessive, e.g., even when water flows out of the soil or when the soil is submerged in water (which is not ordinary case of soil moisture sensing), the capacitance Cx coupled to the first probe 110 may significantly deviate from the initially assumed range (e.g., the difference (ω2−ω1) is positive). In this case, according to an embodiment of the present invention, the first resonant frequency ω1 may have a higher value than the second resonant frequency ω2, and thus the difference between the second resonant frequency ω2 and the first resonant frequency ω1 may have a negative value.

In this case, the determination circuit 120 may determine that detection is inappropriate (not in ordinary case), and may notify the user of an error through a visual or aural means such as a display or a speaker.

Meanwhile, the determination circuit 120 may have a plurality of reference values for the resonant frequency according to a quantitative change in the first resonant frequency ω1. When the difference between the first resonant frequency ω1 and the second resonant frequency ω2 is defined as a first threshold value in the case where the moisture content of the soil is not measured, i.e., in the case where there is no soil surrounding the first electrode 112 of the first probe 110, the determination circuit 120 may consider that a significant change has occurred in the first resonant frequency ω1 if the change value of the first resonant frequency ω1 is equal to or higher than a first threshold value, and may thus determine that the moisture content contained in the soil has a significant value.

Although the second resonance circuit 140 disposed close to the first resonance circuit 130 and having the second capacitor 148 configured to have the same capacitance as the first capacitor 138 so as to have the same impedance, the second inductor 146 configured to have the same inductance as the first inductor 136, and the parasitic resistor 144 configured to have the same resistance value as the first parasitic resistor 134 generates the second electrical signal having the second resonant frequency ω2, which is the reference resonant frequency formed from the second AC signal applied from the second oscillator 142 having the same frequency or phase as the first oscillator 132, there may be a specific difference in frequency between the second electrical signal and the first electrical signal having the first resonant frequency ω1 according to process conditions or various environmental variables.

The determination circuit 120 may set the specific difference in frequency as an offset, may define it as a first threshold value, and may thus consider that a significant change has occurred in the first resonant frequency ω1 only when the difference between the second resonant frequency ω2 and the first resonant frequency ω1 is equal to or higher than the first threshold value and then determine that the moisture content contained in the soil has a significant value.

Alternatively, according to an embodiment of the present invention, the determination circuit 120 may define changes in the first resonant frequency ω1 as a second threshold value, a third threshold value, and a fourth threshold value according to multiples of the first threshold value, and may classify and determine the level of the moisture content contained in the soil.

The determination circuit 120 may further include a control unit/controller/processor (not shown) configured to control the operations of the first oscillator 132 and the first resonance circuit 130 therein. A first AC signal is applied from the first oscillator 132 to the first resonance circuit 130 in response to a control command from the controller, and the determination circuit 120 may receive information about the first resonant frequency ω1 of the first electrical signal formed in the first resonance circuit 130.

Furthermore, the determination circuit 120 may perform a calibration process. The determination circuit 120 may perform a calibration process when the determination circuit 120 does not measure the moisture content of the soil, i.e., when there is no moisture contained in the soil surrounding the outside of the first electrode 112 of the first probe 110. In this case, the first resonance circuit 130 or the second resonance circuit 140 may be adjusted such that the difference between the first resonant frequency ω1 and the second resonant frequency ω2 becomes zero through the calibration process.

The difference between the first resonant frequency ω1, detected in the absence of moisture contained in the soil surrounding the first electrode 112 of the first probe 110, and the second resonant frequency ω2 may be stored in separate memory or storage through the calibration process, and may be processed as offset information in a future soil moisture detection process.

After the calibration, the adjustment of the difference between the first resonant frequency ω1 and the second resonant frequency ω2 may be performed using a means such as the adjustment of the value of the variable resistor R'.

Figure 7:
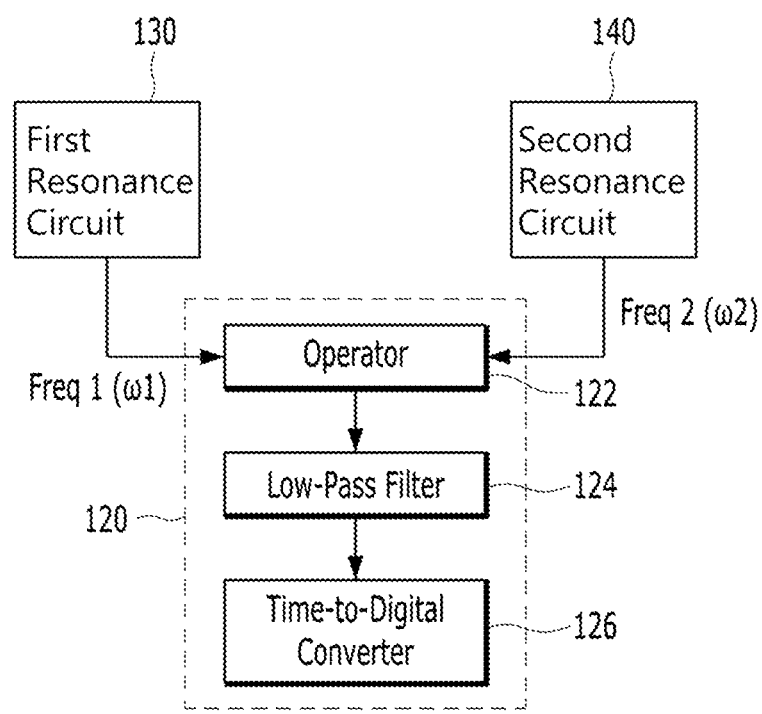
FIG. 7 is a diagram showing the configuration of the determination circuit of a soil monitoring sensor according to an embodiment of the present invention and the interaction among a first resonance circuit, a second resonance circuit, and the determination circuit.

FIG. 7 is a diagram showing the configuration of the determination circuit 120 of soil monitoring sensors 100 and 200 according to embodiments of the present invention and the interaction among a first resonance circuit 130, a second resonance circuit 140, and the determination circuit 120.

FIG. 7 is a diagram showing the signal processing process of the soil monitoring sensors 100 or 200 and a configuration for the signal processing of the determination circuit 120 according to the embodiment of the present invention. The soil monitoring sensor 100 or 200 according to the embodiment of the present invention includes the first resonance circuit 130, the second resonance circuit 140, and the determination circuit 120.

The descriptions of the operations of the first resonance circuit 130, the second resonance circuit 140, and the determination circuit 120 of FIG. 7 that overlap the foregoing descriptions will be omitted.

In FIG. 7, the determination circuit 120 includes an operator circuit 122, a low-pass filter 124, and a time-to-digital converter 126.

The operator circuit 122 obtains the difference between the first resonant frequency ω1 and the second resonant frequency ω2. As an example of the simplest method for obtaining the difference between the first resonant frequency ω1 and the second resonant frequency ω2, there may be a method in which the operator circuit 122 multiplies the first resonant frequency ω1 and the second resonant frequency ω2. The low-pass filter 124 is connected to the output terminal of the calculator 122, and removes high-frequency components. Accordingly, the low-frequency signal of a third frequency component corresponding to the difference between the first resonant frequency ω1 and the second resonant frequency ω2 is generated.

The time-to-digital converter 126 is connected to the output terminal of the low-pass filter 124, and digitally counts the frequency of the third frequency component signal. In this case, the time-to-digital converter 126 may output a digitized value proportional to the frequency of the third frequency component signal.

According to an embodiment, the time-to-digital converter 126 may generate a pulse signal having a fourth frequency proportional to the frequency of the third frequency component signal of the third frequency component signal. Although the fourth frequency may be the same as the frequency of the third frequency component signal, the fourth frequency may become a frequency different from a first frequency due to the influence of a transfer function reflected via the operator circuit 122 and the low-pass filter 124. The time-to-digital converter 126 may count the number of pulses of the pulse signal having the fourth frequency for a predetermined time period, or may generate a digital count value for the pulse width or period of the pulse signal having the fourth frequency.

The digitized count value generated by the determination circuit 120, i.e., a digitized value proportional to the frequency of the third frequency component signal, may be converted into an analog signal proportional to the digitized value again according to the configuration of the soil monitoring sensor 100 or 200, and may be transmitted to the main processor side of the soil monitoring sensor 100 or 200. In this case, the voltage, current, frequency, or amplitude of the analog signal may be converted into a value proportional to the frequency of the third frequency component signal.

The first threshold value and the second threshold value applied in the determination circuit 120 of the previous embodiment may be applied to digital count values generated as the output of the time-to-digital converter 126. According to an embodiment of the determination circuit 120, a sampler and a comparator for the third frequency component signal may be included. In this case, for the smooth operation of the determination circuit 120, the sampler and the comparator may be designed by selecting an operating frequency sufficiently higher than the frequency component corresponding to the second threshold value.

The time it takes for the conventional soil monitoring sensor to determine the moisture contained in the soil is about hundreds of milliseconds to a few seconds. The process of determining the moisture content of the soil according to the present invention may detect a complete result within hundreds of microseconds to a few milliseconds. As described above, since the soil monitoring sensors 100 and 200 according to the present invention use the time-to-digital converter instead of a PLL loop, the stable operation of the circuit is possible without a control loop, the manufacturing cost is low, and the implementation of the constituent circuits is simple.

The determination circuit 120 of the present invention may generate a determination result as a separate signal by applying the first threshold value and the second threshold value to the digital count value, and may transmit it to the main processor of the soil monitoring sensors 100 and 200.

The main processor may detect that the moisture content contained in the soil has a significant value in the case of the first threshold value, and may determine that the moisture content contained in the soil has a larger value in the case of the second threshold value. In addition, the level of the moisture content contained in the soil may be determined according to a plurality of threshold values set as a plurality of set reference values. In an embodiment of the present invention, the second threshold may be larger than the first threshold.

Figure 8:
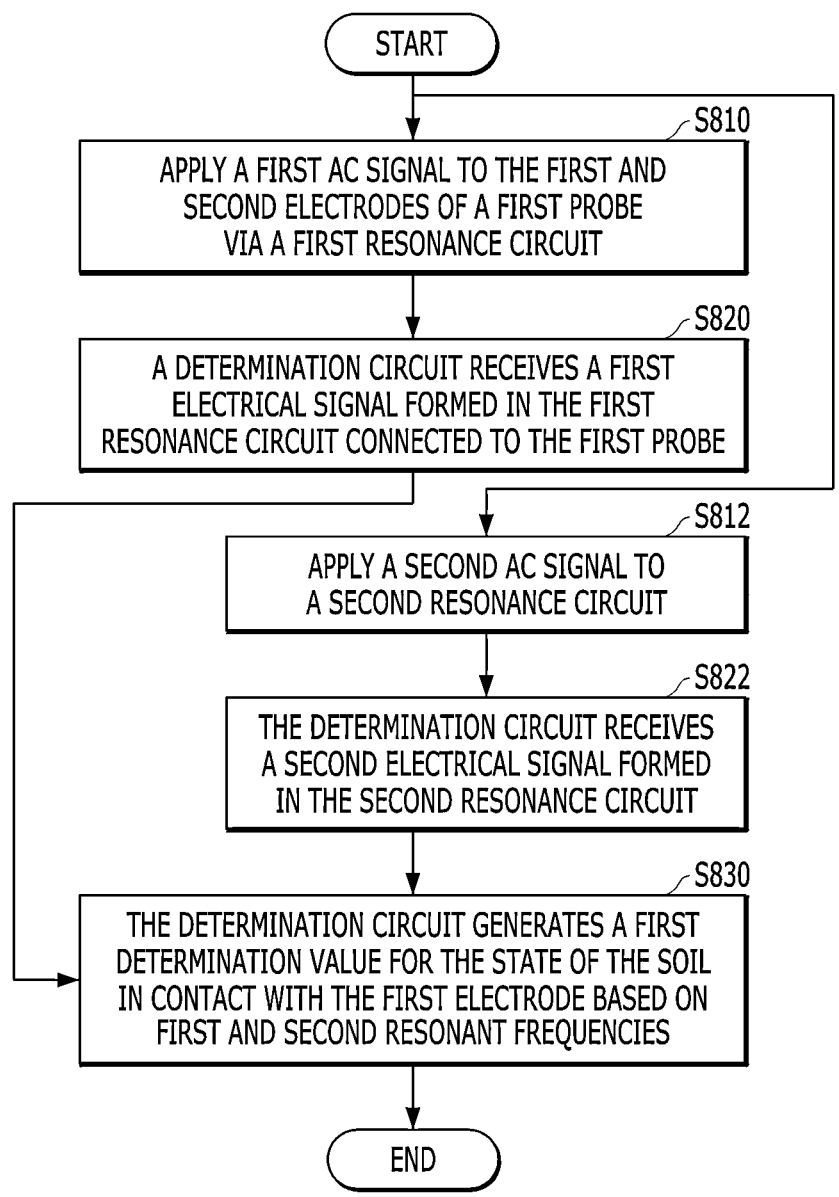
FIG. 8 is an operational flowchart showing an embodiment of a method of operating the soil monitoring sensor of FIG. 1.

FIG. 8 is an operational flowchart showing an embodiment of a method of operating the soil monitoring sensor 100 of FIG. 1.

The soil moisture detection method of the present invention may be implemented by the soil monitoring sensor 100 of FIG. 1 or a control unit (not shown) therein.

Referring to FIG. 8, a first AC signal is applied to the first electrode 112 and second electrode 114 of the first probe 110 and the first resonance circuit 130 by the first oscillator 132 at step S810. The operation of the first oscillator 132 or the operation of applying the first AC signal may be controlled by the control unit/controller/processor (not shown).

Due to the application of the first AC signal, a first electrical signal is formed in the first resonance circuit 130. The first resonance circuit 130 connects the determination circuit 120 and the first probe 110 therebetween. The determination circuit 120 receives the first electrical signal having a first resonant frequency $\omega 1$ at step S820.

A second AC signal is applied to the second resonance circuit 140 by the second oscillator 142 at step S812. The operation of the second oscillator 142 or the operation of applying the second AC signal may be controlled by the control unit/controller/processor (not shown).

Due to the application of the second AC signal, a second electrical signal is formed in the second resonance circuit 140, and the determination circuit 120 receives the second electrical signal having a second resonant frequency $\omega 2$ at step S822. Steps S812 and S822 may be performed in parallel with steps S810 and S820.

The determination circuit 120 having received the first electrical signal and the second electrical signal detects the difference between the first resonant frequency $\omega 1$ and the second resonant frequency $\omega 2$ at step S830. The determination circuit 120 determines whether the moisture content contained in the soil surrounding the outside of the first electrode 112 of the first probe 110 has a significant value based on the difference between the first resonant frequency $\omega 1$ and the second resonant frequency $\omega 2$.

When the determination circuit 120 does not determine that the moisture content contained in the soil surrounding the outside of the first electrode 112 of the first probe 110 has a significant value, the current process is terminated. If necessary, step S810 may be repeated again after a certain period of time has elapsed or when a predetermined condition is satisfied.

When the determination circuit 120 determines that the moisture content contained in the soil surrounding the outside of the first electrode 112 of the first probe 110 has a significant value, the determination circuit 120 determines the moisture content contained in the soil from the first probe 110 based on the difference between the first resonant frequency $\omega 1$ and the second resonant frequency $\omega 2$ at step S830.

Figure 9:
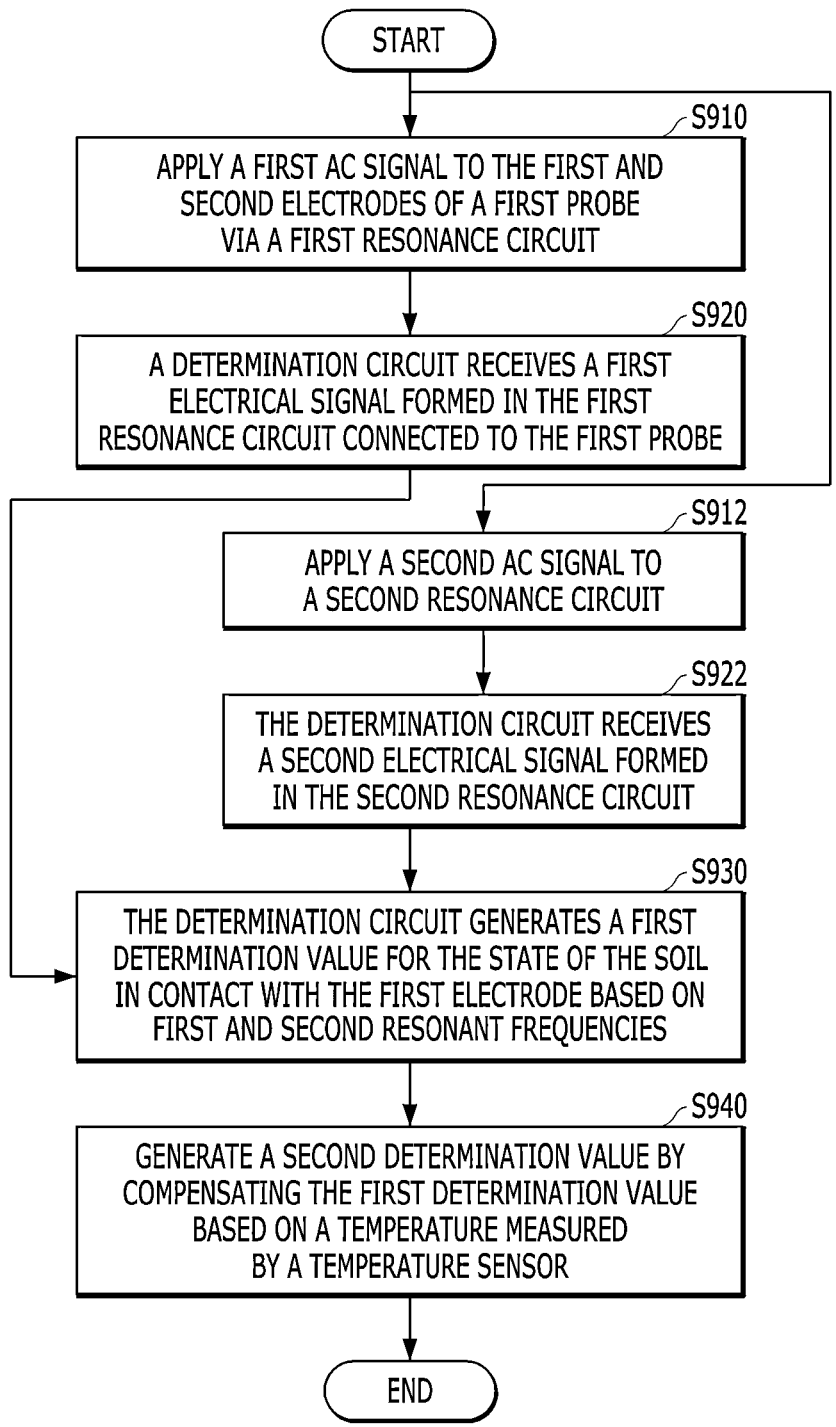
FIG. 9 is an operational flowchart showing an embodiment of a method of operating the soil monitoring sensor of FIG. 2.

FIG. 9 is an operational flowchart showing an embodiment of a method of operating the soil monitoring sensor of FIG. 2. The soil moisture detection method of the present invention may be implemented by each of the soil monitoring sensors 100 and 200 of FIGS. 1 and 2, or a control unit/controller/processor (not shown) therein.

Referring to FIG. 9, a first AC signal is applied to the first probe 110 by the first oscillator 132 via the first resonance circuit 130 at step S910. Furthermore, the determination circuit 120 receives a first electrical signal formed in the first resonance circuit 130 connected to the first probe 110 and having a first resonant frequency $\omega 1$ at step S920.

A second AC signal is applied to the second resonance circuit 140 by the second oscillator 142 at step S912. Furthermore, the determination circuit 120 receives a second electrical signal formed in the second resonance circuit 140 and having a second resonant frequency $\omega 2$ at step S922. Steps S912 and S922 may be performed in parallel with steps S910 and S920.

The determination circuit 120 may generate a first determination value based on the first resonant frequency $\omega 1$ of the first electrical signal and the second resonant frequency $\omega 2$ of the second electrical signal at step S930. The determination circuit 120 may generate a second determination value by compensating the first determination value based on the temperature measured by the temperature sensor 250 at step S940.

In the embodiments of FIGS. 1 to 9, the temperature sensor 250 may utilize a known temperature sensor in various ways. One of the widely known methods of measuring temperature is to use a negative temperature coefficient (NTC) material. Since values such as resistance will vary based on temperature, the temperature may be calculated by detecting a change in the electrical signal such as voltage or current using this.

The determination circuit 120 may calculate the permittivity of water based on the measured temperature, and may calculate a compensated capacitance value based on a measured frequency shift and the temperature compensated permittivity of water. The determination circuit 120 may calculate the moisture content or water content of the soil or a medium (a medium in which the crop grows) based on the compensated capacitance value.

In this case, the moisture content, the water content, and/or capacitance value may be given as a function of the temperature and the shift of a resonant frequency. Alternatively, the determination circuit 120 may calculate the moisture content or water content of the soil based on the temperature based on predetermined and pre-stored table information. The table information may store the temperature and information about relationships with other variables. For example, other variables that may be contrasted with temperature may include at least one of a moisture content, a capacitance value, a change in impedance, and the shift of a resonant frequency.

Figure 10:
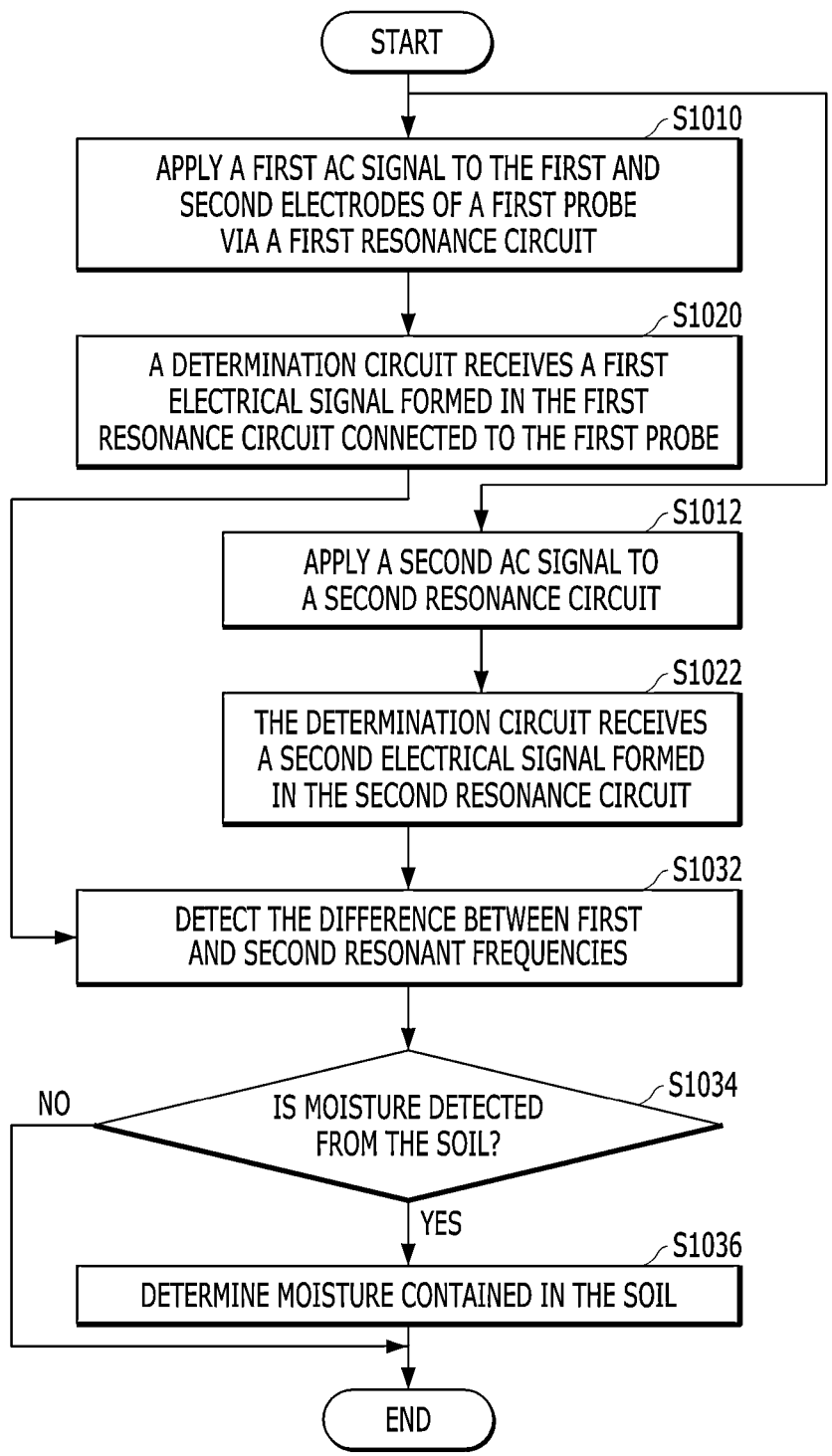
FIG. 10 is an operational flowchart showing an embodiment of a method of operating the soil monitoring sensor of FIG. 7.

FIG. 10 is an operational flowchart showing an embodiment of a method of operating the soil monitoring sensor 100 or 200 of FIG. 7. Referring to FIG. 10, steps S1010, S1020, S1012, and S1022 are the same as steps S810, S820, S812, and S822 of FIG. 8, and steps S910, S920, S912, and S922 of FIG. 9, and thus redundant descriptions thereof will be omitted.

Furthermore, the determination circuit 120 detects the difference between the first resonant frequency $\omega 1$ of the first electrical signal and the second resonant frequency $\omega 2$ of the second electrical signal at step S1032.

The determination circuit 120 determines whether the moisture content contained in the soil surrounding the outside of the first electrode 112 of the first probe 110 has a significant value based on the difference between the first resonant frequency $\omega 1$ and the second resonant frequency $\omega 2$ at step S1034.

When the determination circuit 120 does not determine that the moisture content contained in the soil surrounding the outside of the first electrode 112 of the first probe 110 has a significant value, the current process is terminated. If necessary, a process starting from step S1010 may be repeated again after a certain period of time has elapsed or when a predetermined condition is satisfied.

When the determination circuit 120 determines that the moisture content contained in the soil surrounding the outside of the first electrode 112 of the first probe 110 has a significant value, the determination circuit 120 determines the moisture content contained in the soil from the first probe 110 based on the difference between the first resonant frequency ω1 and the second resonant frequency ω2, which is a reference resonant frequency for the surface layer of the soil from the second probe 210, at step S1036.

Figure 11:
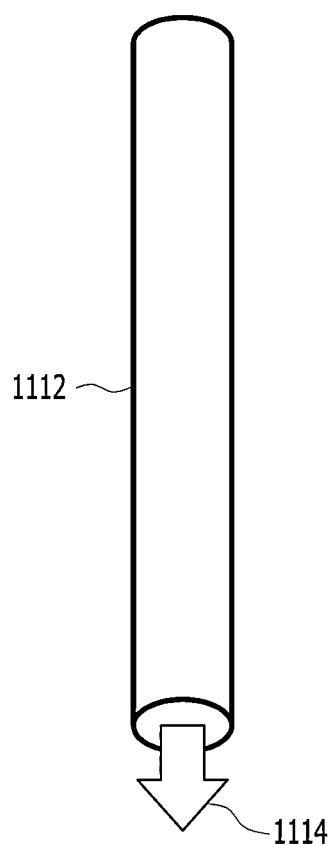
FIG. 11 is a diagram showing an embodiment of the outer shape of the single-pole probe shown in FIGS. 3 and/or 4.

FIG. 11 is a diagram showing an embodiment of the outer shape of the single-pole probe 110 shown in FIGS. 3 and/or 4.

Referring to FIG. 11, there are shown a first electrode 1112 surrounding the outside of the single-pole probe 110 and a second electrode 1114 protruding from the tip of the single-pole probe 110 and coming into contact with the soil. The first electrode 1112 may be formed to extend in a first direction in which the single pole probe 110 penetrates the soil, and may be formed to surround the overall surface of the outside of the single pole probe 110, or to monitor deep soil. When the monitoring of the deep soil is focused on, the first electrode 1112 may be formed to surround only a part of the outer side of the single-pole probe 110. In FIG. 11, the outer shape of the single-pole probe 110 is implemented in the form of a round bar, but embodiments of the present invention are not limited to this embodiment.

Figure 12:
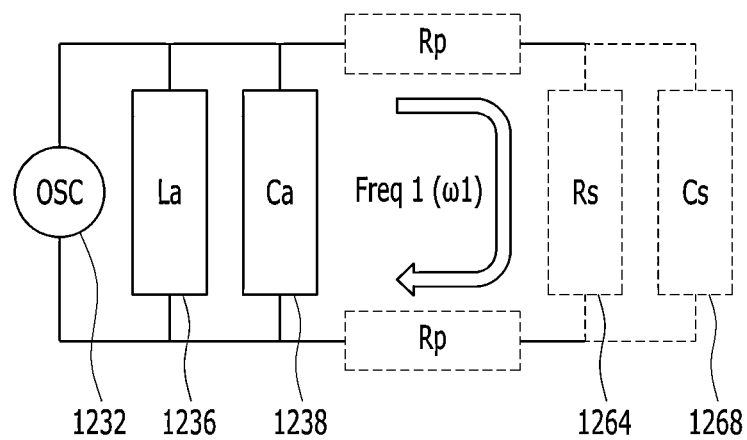
FIG. 12 is a diagram showing an equivalent circuit for illustrating the operating principle of a soil monitoring sensor according to an embodiment of the present invention.

FIG. 12 is a diagram showing an equivalent circuit for illustrating the operating principle of a soil monitoring sensor according to an embodiment of the present invention.

A first oscillator 1232 applies a first AC signal to a first inductor 1236 and a first capacitor 1238 that form a first resonance circuit. The parasitic resistance exhibited by a first electrode wiring connecting the first resonance circuit and a first probe and/or a second electrode wiring is represented by Rp in FIG. 12. As a parasitic capacitance Cs 1268, exhibited in the first electrode by the interaction between the soil and the first electrode of the first probe, and a parasitic resistance Rs are combined with the parasitic resistance Rp of the wirings and the impedance of the first inductor 1236 and the first capacitor 1238, the combined impedance of the soil monitoring sensor 100 of FIG. 12 is formed. The first resonant frequency ω1 of the first electrical signal formed in the equivalent circuit of FIG. 12 is determined based on this combined impedance.

In general, it is known that the parasitic capacitance Cs 1268 has a strong influence on a change in impedance in a high-frequency signal environment and is influenced by the moisture of the soil. It is known that the parasitic resistance Rs 1264 has a strong influence on a change in impedance in a relatively low-frequency environment and is influenced by the electrical conductivity of the soil.

In an embodiment of the present invention, the determination circuit 120 may measure the moisture of the soil using a frequency component of a few hundred MHz band, and may measure the electrical conductivity of the soil using a frequency component of a few MHz or a few hundreds of kHz band. In this case, a channel/routine for measuring the moisture of the soil and a channel/routine for measuring the electrical conductivity of the soil may be separately performed. Alternatively, the moisture and electrical conductivity of the soil may simultaneously be obtained by analyzing an electrical signal obtained by a single channel/routine.

Meanwhile, in an embodiment of the present invention, the determination circuit 120 may measure the moisture of the soil using the difference between resonant frequencies, and may detect the electrical conductivity of the soil by comparing and analyzing the amplitudes of resonance signals between a reference resonance circuit and a sensor-side resonance circuit based on the parasitic resistance Rp of the wirings. In this case, the electric conductivity may be detected by determining that a change in the amplitude of an electrical signal between both ends of the first oscillator 1232 or the first inductor 1236 and the first capacitor 1238 is proportional to a change in electric conductivity. Even in this case, a channel/routine for measuring the moisture of the soil and a channel/routine for measuring the electrical conductivity of the soil may be separately executed. Alternatively, the moisture and electrical conductivity of the soil may simultaneously be obtained by analyzing an electrical signal obtained by a single channel/routine.

In an embodiment of the present invention, the determination circuit 120 may detect the difference between resonant frequencies using a frequency component of a few hundred MHz band and measure the moisture of the soil, and may detect a change in the amplitude of a resonance signal by using a frequency component of a few MHz or a few hundreds of kHz band and measure the electrical conductivity of the soil. Even in this case, a channel/routine for measuring the moisture of the soil and a channel/routine for measuring the electrical conductivity of the soil may be separately executed. Alternatively, the moisture and electrical conductivity of the soil may simultaneously be obtained by analyzing an electrical signal obtained by a single channel/routine.

The method of operating a circuit according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

According to the present invention, high-frequency signals are generated in the circuit having a capacitance formed in a probe for a soil monitoring sensor using the soil as a medium and the circuit having a reference capacitance, respectively, frequencies for the high-frequency signals in the two circuits are measured and compared, and the moisture content in the soil is quantified, thereby enabling the moisture state of the soil to be more accurately and rapidly determined in real time.

Furthermore, according to the present invention, the soil monitoring sensor may be used non-destructively and semi-permanently, and the stability of the solid monitoring sensor may be ensured.

Furthermore, according to the present invention, when the determination circuit of the soil monitoring sensor is fabricated using a single chip, the sensor circuit and the reference resonance circuit are disposed close to each other, and the same type of devices may be used for the fabrication, so that a measurement error attributable to process variation may be reduced, thereby enabling the moisture content of the soil to be accurately determined in real time.

The soil monitoring sensor according to the present invention may further include a temperature sensor in order to more accurately detect the moisture content of the soil, and may measure precise moisture content by compensating the moisture content of the soil based on the temperature sensor.

The soil monitoring sensor according to the present invention may monitor characteristic parameters such as the moisture and salts of the soil surrounding the outer periphery of the probe by means of the single-pole probe. Accordingly, the soil monitoring sensor according to the present invention does not limit the range of the soil to be monitored, and is applicable to the soils in various environments.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A soil monitoring sensor comprising:
    a first probe formed to extend in a first direction so as to penetrate into a soil, and including a first electrode and a second electrode;
    a first resonance circuit connected to the first electrode and the second electrode of the first probe, and configured such that a first alternating current (AC) signal is applied thereto;
    a second resonance circuit having a same impedance as the first resonance circuit, and configured such that a second AC signal, which is a reference AC signal and has a same characteristic as the first AC signal, is applied thereto; and
    a determination circuit configured to:
        receive a first electrical signal formed in the first resonance circuit;
        receive a second electrical signal formed in the second resonance circuit; and
        generate a first determination value for a state of the soil based on a first resonant frequency of the first electrical signal and a second resonant frequency of the second electrical signal,
    wherein the first electrode includes a conductor surrounding an outside of the first probe, comes into contact with the soil, and detects information about the state of the soil,
    wherein the second electrode is disposed inside the first probe, protrudes from a tip of the first probe to come into contact with the soil, and is connected to a ground node of at least one of the first resonance circuit, the second resonance circuit, and the determination circuit to function as a ground electrode, and
    wherein the first electrode comes into contact with the soil outside the first probe, and an area in which the first electrode comes into contact with the soil is larger than an area in which the second electrode comes into contact with the soil.

2. The soil monitoring sensor of claim 1, further comprising a temperature sensor coupled to at least any one of the first electrode and the second electrode of the first probe,
    wherein the determination circuit is further configured to generate a second determination value for the state of the soil by compensating the first determination value based on a temperature measured by the temperature sensor.

3. The soil monitoring sensor of claim 1, wherein a gap between the first electrode and the second electrode is filled with an insulator, or the first electrode and the second electrode are spaced apart from each other so that an empty space is formed inside the first probe.

4. The soil monitoring sensor of claim 1, wherein the determination circuit is further configured to:
    detect a quantitative change in the first resonant frequency of the first electrical signal formed in the first resonance circuit based on a capacitance formed between the soil surrounding and being in contact with the first electrode and the first electrode due to moisture contained in a region of the soil, surrounding and being in contact with the first electrode, adjacent to the first electrode; and
    generate the first determination value for the state of the soil based on the detected quantitative change in the first resonant frequency.

5. The soil monitoring sensor of claim 1, wherein the determination circuit is further configured to:
    detect a difference between the second resonant frequency, which is a reference resonant frequency of the second electrical signal formed in the second resonance circuit under an influence of the second AC signal applied to the second resonance circuit, and the first resonant frequency; and
    generate the first determination value for the state of the soil based on the difference between the second resonant frequency and the first resonant frequency.

6. The soil monitoring sensor of claim 5, wherein the determination circuit is further configured to, when the difference between the second resonant frequency and the first resonant frequency is equal to or higher than a first threshold value, consider that a significant change has occurred in the first resonant frequency and determine the state of the soil.

7. The soil monitoring sensor of claim 1, wherein the determination circuit comprises:
    an operator circuit configured to obtain a difference between the first resonant frequency and the second resonant frequency;
    a low-pass filter connected to an output terminal of the operator, and configured to remove a high-frequency component; and
    a time-to-digital converter connected to an output terminal of the low-pass filter, and configured to digitally count a frequency of a third frequency component signal corresponding to the difference between the first resonant frequency and the second resonant frequency.

8. A soil monitoring method comprising:
    applying, by a first oscillator, a first alternating current (AC) signal to a first electrode and a second electrode of a first probe via a first resonance circuit connected to the first electrode and the second electrode of the first probe formed to extend in a first direction so as to penetrate into a soil and including the first electrode and the second electrode;

applying, by a second oscillator having a same characteristic as the first oscillator, a second AC signal, which is a reference AC signal, to a second resonance circuit having a same impedance as the first resonance circuit;

receiving, by a determination circuit, a first electrical signal formed in the first probe and the first resonance circuit under an influence of the first AC signal;

receiving, by the determination circuit, a second electrical signal formed in the second resonance circuit under an influence of the second AC signal applied to the second resonance circuit; and generating, by the determination circuit, a first determination value for a state of the soil in contact with the first electrode surrounding an outside of the first probe based on a first resonant frequency of the first electrical signal and a second resonant frequency of the second electrical signal; and detecting, by the determination circuit, a difference between the first resonant frequency and the second resonant frequency, wherein the generating a first determination value comprises generating the first determination value for moisture contained in a region of the soil, in contact with the first electrode, adjacent to the first electrode based on the difference between the first resonant frequency and the second resonant frequency.

9. The soil monitoring method of claim 8, further comprising:

measuring, by a temperature sensor coupled to any one of the first electrode and the second electrode of the first probe, a temperature of the soil; and generating a second determination value for the state of the soil by compensating the first determination value based on the temperature measured by the temperature sensor.

10. The soil monitoring method of claim 8, wherein the generating a first determination value comprises:

detecting a quantitative change in the first resonant frequency of the first electrical signal formed in the first resonance circuit based on a capacitance formed between the soil, surrounding and being in contact with the first electrode, and the first electrode due to moisture contained in a region of the soil, surrounding and being in contact with the first electrode, adjacent to the first electrode; and generating the first determination value for the state of the soil based on the detected quantitative change in the first resonant frequency.

11. The soil monitoring method of claim 8, wherein the detecting a difference between the first resonant frequency and the second resonant frequency comprises:

obtaining, by an operator circuit, the difference between the first resonant frequency and the second resonant frequency;

removing, by a low-pass filter connected to an output terminal of the operator circuit, a high-frequency component of an output signal of the operator circuit; and generating, by a time-to-digital converter connected to an output terminal of the low-pass filter, the difference between the first resonant frequency and the second resonant frequency as a digital value by digitally counting a frequency of a third frequency component signal corresponding to the difference between the first resonant frequency and the second resonant frequency.

\* \* \* \* \*